United States Patent
Crook et al.

(10) Patent No.: US 6,485,467 B1
(45) Date of Patent: *Nov. 26, 2002

(54) EXTRACORPOREAL PNEUMOPERITONEUM ENCLOSURE AND METHOD OF USE

(75) Inventors: Berwyn M. Crook, Yardley, PA (US); Robert D. Rambo, Sellersville, PA (US); Thomas E. Lyons, Quakertown, PA (US); Frederic C. Feiler, Jr., Raleigh, NC (US)

(73) Assignees: Medical Creative Technologies, Inc., Colmar, PA (US); Dexterity Surgical, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/367,753

(22) PCT Filed: Oct. 8, 1997

(86) PCT No.: PCT/US97/18168

§ 371 (c)(1), (2), (4) Date: Feb. 23, 2000

(87) PCT Pub. No.: WO98/35614

PCT Pub. Date: Aug. 20, 1998

(51) Int. Cl.[7] ............................................. A61M 5/32
(52) U.S. Cl. ..................... 604/174; 604/99.01; 604/338
(58) Field of Search .................. 604/174, 99.01, 604/338, 180, 337, 167.01, 167.03, 27, 236, 256; 600/21, 22, 207; 606/1, 201–203, 213, 215, 192, 198; 128/850–856, 846, 897

(56) References Cited

U.S. PATENT DOCUMENTS

| | | | |
|---|---|---|---|
| 4,069,913 A | 1/1978 | Harrigan | 206/278 |
| 4,436,519 A | 3/1984 | O'Neill | 604/175 |
| 4,485,490 A | 12/1984 | Akers et al. | 2/2 |
| 4,964,174 A | 10/1990 | Martin | 2/161 R |
| 4,998,538 A | 3/1991 | Charowsky et al. | 128/856 |
| 5,082,005 A | 1/1992 | Kaldany | 128/850 |
| 5,366,478 A | 11/1994 | Brinkerhoff et al. | 660/213 |
| 5,370,625 A | 12/1994 | Schichman | 604/174 |
| 5,402,536 A | 4/1995 | Matthews | 2/16 |
| 5,437,683 A | 8/1995 | Neumann et al. | 606/151 |
| 5,480,410 A | 1/1996 | Cuschieri et al. | 606/213 |
| 5,514,133 A | 5/1996 | Golub et al. | 606/1 |
| 5,522,791 A | 6/1996 | Leyva | 600/207 |
| 5,636,645 A | 6/1997 | Ou | 128/898 |
| 5,640,977 A | 6/1997 | Leahy et al. | 128/897 |
| 5,653,705 A | 8/1997 | de le Torre et al. | 606/1 |
| 5,672,168 A | 9/1997 | de le Torre et al. | 606/1 |
| 5,720,759 A | 2/1998 | Green et al. | 606/167 |
| 5,741,298 A | 4/1998 | MacLeod | 606/213 |
| 5,813,409 A * | 9/1998 | Leahy et al. | 128/850 |
| 5,899,208 A * | 5/1999 | Bonadio | 128/850 |
| 5,906,577 A | 5/1999 | Beane et al. | 600/207 |
| 6,033,426 A * | 3/2000 | Kaji | 600/207 |
| 6,142,936 A * | 11/2000 | Beane et al. | 600/206 |
| 6,254,534 B1 * | 7/2001 | Butler et al. | 600/206 |
| 2002/0045796 A1 * | 4/2002 | O'Connor et al. | 600/21 |

* cited by examiner

*Primary Examiner*—Henry Bennett
*Assistant Examiner*—Kathryn Ferko
(74) *Attorney, Agent, or Firm*—Howson and Howson

(57) ABSTRACT

Surgical apparatus for providing extracorporeal pneumoperitoneum. One embodiment provides a reversely turned fluid and gas impermeable fingerless sleeve (14) with a quick connect and disconnect assembly around the cuff of the sleeve (14) for sealing around an abdominal incision to allow hand-assisted minimally invasive surgery under conditions of pneumoperitoneum. A dome shaped enclosure (62) is provided for use with the quick connect and disconnect assembly to seal around an abdominal incision and maintain pneumoperitoneum during interruptions in a surgical procedure. Another embodiment incorporates a fingerless sleeve (14) which is adhesively secured directly to a patient's skin around an incision. The sleeve is applied over a pre-gloved surgeon's hand, and an outer surgical glove (18) is applied over the sleeve (14) in the region where the fingers and thumb protrude before the sleeve (14) is reversely turned on itself for connection to a patient.

37 Claims, 7 Drawing Sheets

EXTRACORPOREAL PNEUMOPERITONEUM ENCLOSURE AND METHOD OF USE

CROSS-REFERENCE TO RELATED APPLICATIONS

This is a 371 of PCT/US97/18168, filed Oct. 8, 1997, which claims the benefit of the priority of U.S. patent application Ser. No. 08/801,752, filed Feb. 18, 1997.

FIELD OF THE INVENTION

The present invention relates generally to an apparatus and method suitable for maintaining extracorporeal pneumoperitoneum at an abdominal fenestration during surgery, and more particularly to a quick connect and disconnect enclosure and method for insertion of instruments or a surgeon's hand into the body cavity through a fenestration for access to organs and instruments within the cavity without loss of insufflation pressure.

BACKGROUND OF THE INVENTION

Laparoscopy and endoscopy have become a preferred surgical procedure because it is minimally invasive of the patient's body and, in many instances, can be performed in short-procedure facilities with minimal trauma and significantly reduced recuperation time. In some cases, a new procedure referred to as hand-assisted laparoscopy, or endoscopy, has been employed in which a small muscle splitting incision is made just large enough for admitting the surgeon's hand into the abdominal cavity to enable palpation of organs and manipulation of surgical instruments, and to provide bio-physical feedback. Visual feedback is usually provided as well through an endoscope and TV monitor.

Several medical devices have been developed which make it possible for hand-assisted laparoscopy to be carried out in the abdominal cavity while under conditions of pneumoperitoneum. One device, for instance, by Patrick F. Leahy et al. disclosed in U.S. patent application Ser. No. 08/300,346 filed Mar. 29, 1995 (International Application PCT/US95/04202 published Oct. 29, 1995) provides a gas-tight sleeve which communicates with the abdominal cavity through an incision allowing the surgeon's hand access through entry and exit openings at opposite ends of the sleeve. The exit opening is sealed around the incision by a flange adhesively attached to the external surface of the abdomen. After the hand is passed through the entry opening, the sleeve is sealed around the surgeon's forearm by an adjustable cuff. A duckbill check valve disposed between the entry and exit openings forms with the exit opening a substantially gas-tight chamber which allows the surgeon to withdraw his hand from the insufflated cavity with only a slight drop in gas pressure which can be quickly restored.

Another device disclosed in U.S. Pat. No. 5,480,410 to Cuschieri et al. provides a gas-tight enclosure in which a resilient ring at an exit opening is squeezed by hand into an oblong shape for insertion through the abdominal incision, then allowed to expand to its original shape under the edge of the incision to seal the peritoneum and enclosure for sufflation. At least one entry opening is provided for passing an instrument or a surgeon's hand into the enclosure. The enclosure may also include a surgical glove integrally sealed to the entry opening in a glove-box manner for allowing the surgeon's hand sterile access through the exit opening to organs and instruments within the abdominal cavity.

None of these devices, however, satisfies the need for such a gas-tight enclosure which can be quickly disconnected and reconnected as often as necessary during hand-assisted laparoscopic or endoscopic surgery while the enclosure remains sealed in place around the surgeon's hand, and which can maintain abdominal pneumoperitoneum during extended interruptions in an operation for other medical procedures.

OBJECTS OF THE INVENTION

Accordingly, it is an object of the present invention to provide a gas-tight extracorporeal pneumoperitoneum enclosure which is worn by the surgeon during hand-assisted laparoscopic or endoscopic surgery, which can be quickly disconnected from a patient as often as necessary in the course of an operation and reconnected while still sealed around the surgeon's hand, which allows the surgeon to manipulate or palpate organs and instruments from within the abdominal cavity, and which provides bio-physical feedback from the surgeon's hand under conditions of pneumoperitoneum.

Another object of the invention is to provide a surgical apparatus which can be continuously sealed around the surgeon's hand and forearm and selectively connected around an open wound while maintaining pneumoperitoneum in the course of a hand-assisted laparoscopic or endoscopic operation, and which will maintain pneumoperitoneum within the body cavity during any interruptions for any other medical procedure in the course of an operation.

A still further object of the invention is to enable minimally invasive surgery with minimal risk of damage to the immune system, and with shorter healing time and less time needed for recuperation in a hospital.

A further object is to provide a disposable surgical device which is relatively simple in design and easy to use.

SUMMARY OF THE INVENTION

More specifically, in one embodiment, the extracorporeal pneumoperitoneum enclosure is a fluid and gas impermeable elongate fingerless sleeve having an open proximal end and a distal end with holes arranged to seal gas-tightly around the base of the surgeon's thumb and each of the fingers. The sleeve section intermediate its ends is reversely-turned on itself before its proximal end is fastened either directly, or indirectly, onto a patient's skin around an incision. Preferably, a quick connect and disconnect assembly at the proximal end of the sleeve gas-tightly seals to the skin around an incision allowing the surgeon to interrupt and resume a hand-assisted laparoscopic surgical procedure under conditions of pneumoperitoneum as often as needed without removing the sleeve from his/her hand. Integral with the quick connect and disconnect assembly is a pressure relief valve for preventing over-sufflation. At least one instrument port is provided in the cuff for admitting, without loss of gas pressure, surgical instruments.

In another embodiment of the extracorporeal pneumoperitoneum enclosure, a fluid and gas impermeable hemispheric envelope is sealed gas-tightly around the incision. A quick connect and disconnect assembly with integral pressure relief valve is secured around an open base for maintaining the abdominal cavity sufflated during interruptions in an operation. This embodiment also includes a sealable instrument port.

Upper and lower seal rings in both embodiments of the quick connect and disconnect assembly have respectively mating interfaces enabling the sleeve and envelope to be interchangeable without removing the lower seal ring previously attached to a patient.

The method for using the apparatus in a hand-assisted laparoscopic operation is as follows. A lower seal ring of the quick connect and disconnect assembly is adhesively sealed to the skin of the patient around the site where a small muscle-splitting incision is made through the abdomen wall and peritoneum. A wound liner and retractor may be inserted into the incision to protect the wound from contamination and to spread it apart for easier access. Wearing an inner surgical glove, the surgeon inserts his/her hand into the fingerless sleeve until the fingers extend completely through the holes and become tightly sealed around their bases. For extra precaution against leakage, an outer surgical glove is then placed over both the inner glove and the fingerless sleeve. The sleeve is then reversely turned on itself. An upper seal ring of the quick connect and disconnect assembly around the cuff of the glove is then sealingly interconnected with the lower seal ring and the abdomen and glove insufflated to the desired pressure either through a separate cannula or a port in the glove. The surgeon's hand may then be inserted into the abdominal cavity and removed as often as necessary during a laparoscopic procedure. The port in the sleeve permits instruments to be inserted as often as needed. Any increase in sufflating gas pressure, caused by a sudden reduction in volume when inserting the hand, is prevented by the pressure relief valve in the quick connect and disconnect assembly.

Whenever the surgeon wishes to interrupt a surgical procedure while still maintaining pneumoperitoneum, the sleeve is disconnected from the lower seal ring, and in its place the dome-like envelope with upper seal ring are connected to the lower seal ring left on the abdomen and sufflation restored.

Other objects, advantages and novel features of the invention will become apparent from the following detailed description of the invention when considered in conjunction with the accompanying drawings.

DETAILED DESCRIPTION

Figure 1:
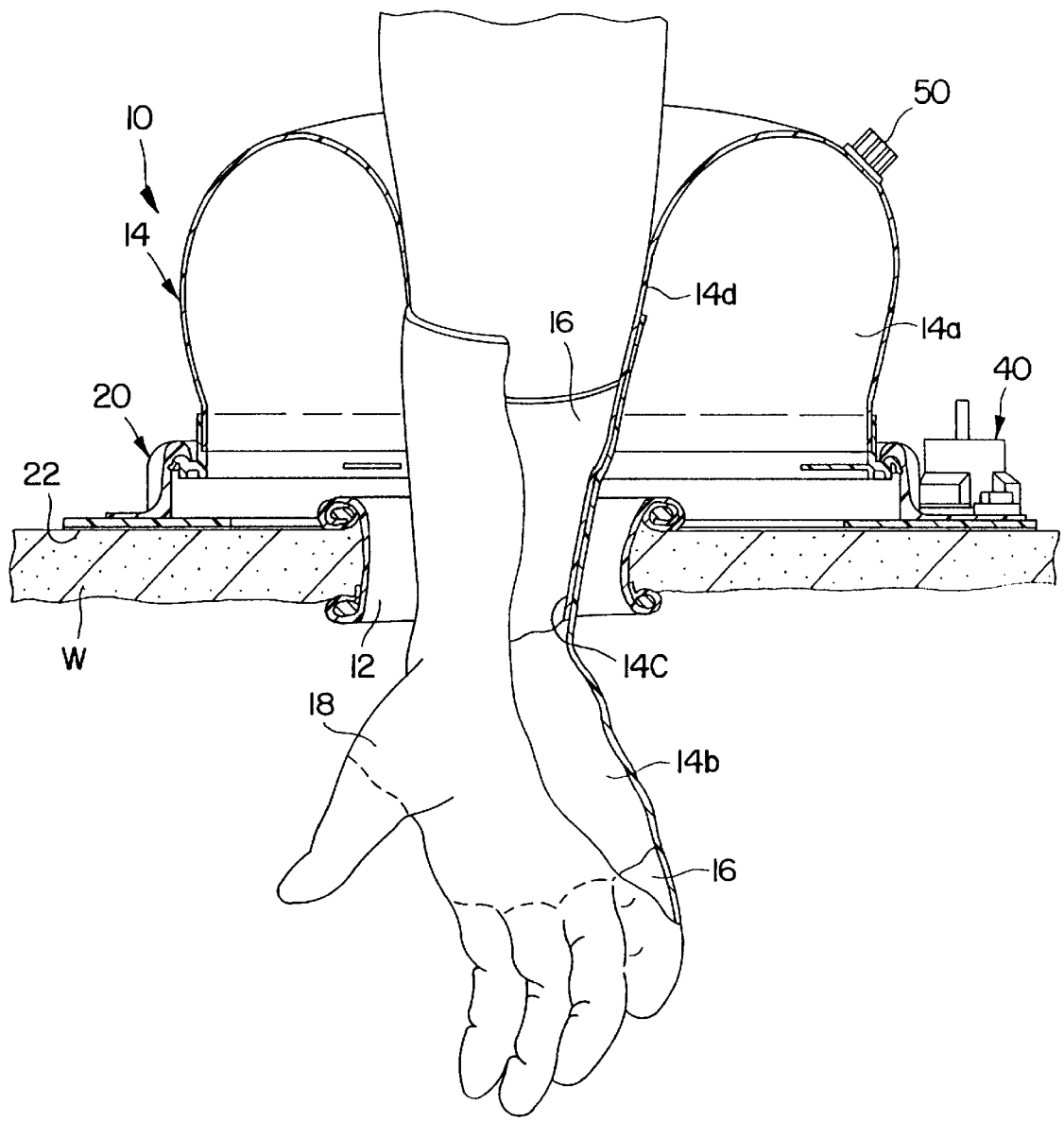
FIG. 1 is a view in elevation and partial cross section of an extracorporeal pneumoperitoneum enclosure, or sleeve, according to one embodiment of the invention as applied in hand-assisted laparoscopic surgery in the abdomen.

Referring now to the drawings, FIG. 1 illustrates an extracorporeal pneumoperitoneum enclosure 10 according to the invention applied to a patient's anterior abdominal wall W. A surgeon's hand extends into the abdominal cavity through a small muscle splitting incision which is protected from wound contamination by a wound protector/retractor 12 such as disclosed in U.S. Pat. No. 5,524,644 to Berwyn M. Crook.

In one preferred embodiment, enclosure 10 includes an elongate gas impermeable flexible sleeve 14 of sufficient length to receive the hand and forearm of the surgeon. Sleeve 14 has an intermediate section that extends from a proximal end cuff section 14a to a "fingerless," distal, hand section 14b where it terminates with holes 15 positioned to receive the full length of the surgeon's thumb and fingers and to seal the sleeve snugly around the root of each as shown in FIG. 2.

Figure 2:
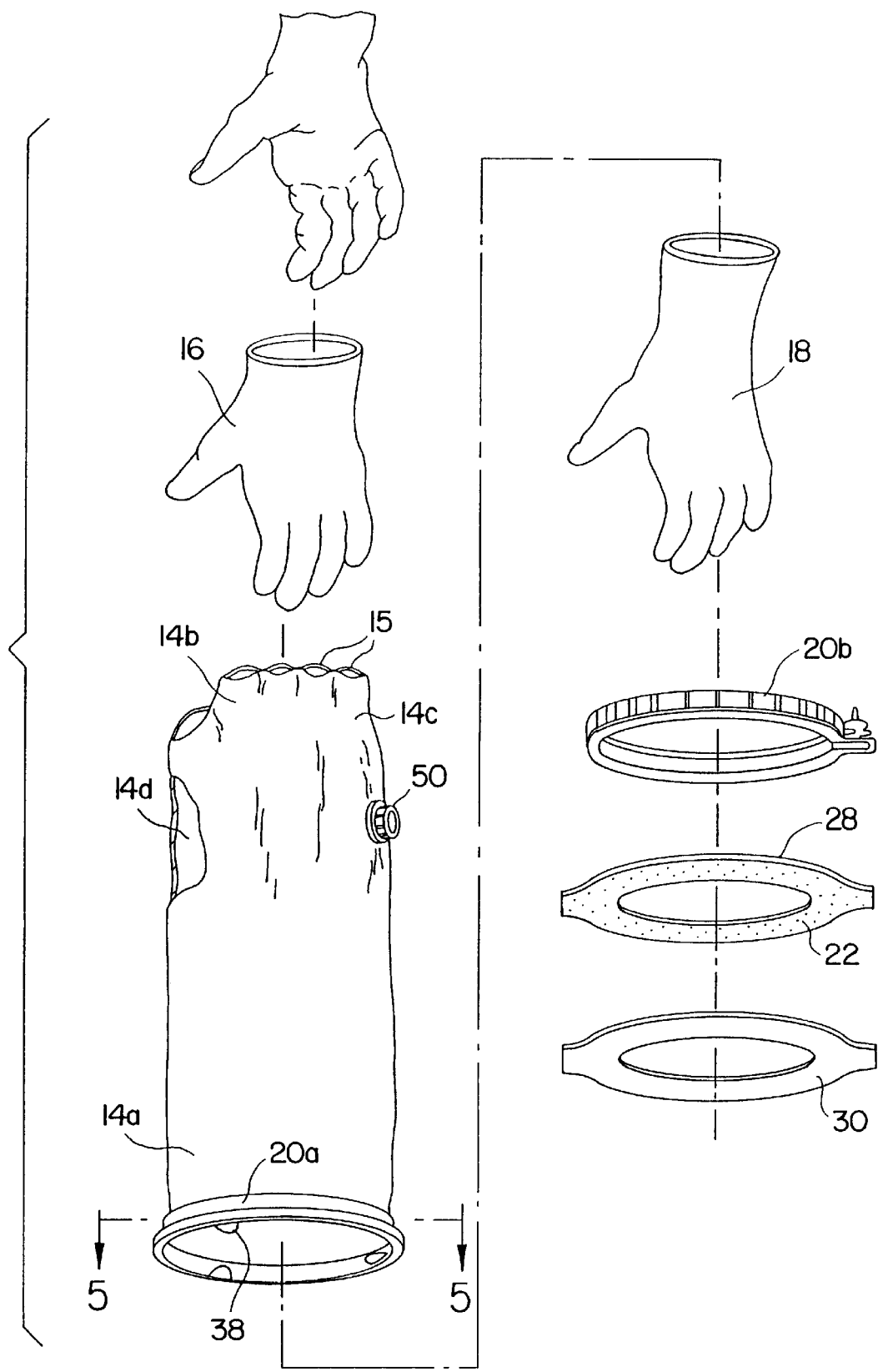
FIG. 2 is perspective view of various components of the sleeve, or enclosure, of FIG. 1 spatially arranged in order of assembly.

As best seen in FIG. 2, sleeve 14 has an inner side 14c which faces outward in FIG. 1 because, in use, the intermediate cuff section is inverted, or reversely-turned on itself, so that the inside faces out. An inner surgical glove 16, worn in direct contact with the hand, is contiguous with inner side 14c, and an outer surgical glove 18, worn to ensure against leakage at holes 15, covers an outer side 14d. Thus, the distal end portion 14b of the sleeve 14 is sandwiched between the inner and outer surgical gloves 16 and 18, respectively and thereby secured in place.

Sleeve 14 is made of surgical grade supple transparent material in one size designed to seal around the fingers of a small hand but which will also stretch slightly under plastic deformation with residual elasticity to accommodate larger hands without constricting circulation to the fingers. A suitable material is 2 mil thick polyethylene film such as X-2000 by Pierson Industries. The preferred diameters of the holes 15, in inches, are as follows: thumb 0.98, index finger 0.79, middle finger 0.87, ring finger 0.75, and pinky 0.63.

In the embodiments of FIGS. 1–9, an annular quick connect and disconnect coupling means assembly 20 is permanently sealed around the proximal end of cuff section 14a and removably sealed with an adhesive 22 to the abdominal skin around the protector/retractor 12.

Referring to FIGS. 3–6, coupling assembly 20 includes interconnecting upper and lower seal rings 20a and 20b, preferably molded of a medical grade flexible, slightly resilient thermoplastic rubber of Shore 80A hardness such as Santoprene® made by Advanced Elastomer Systems. Upper ring 20a defines an annular collar 24 permanently sealed around the periphery of cuff section 14a with an upwardly facing annular bead 26 concentrically disposed around collar 24.

Figure 3:
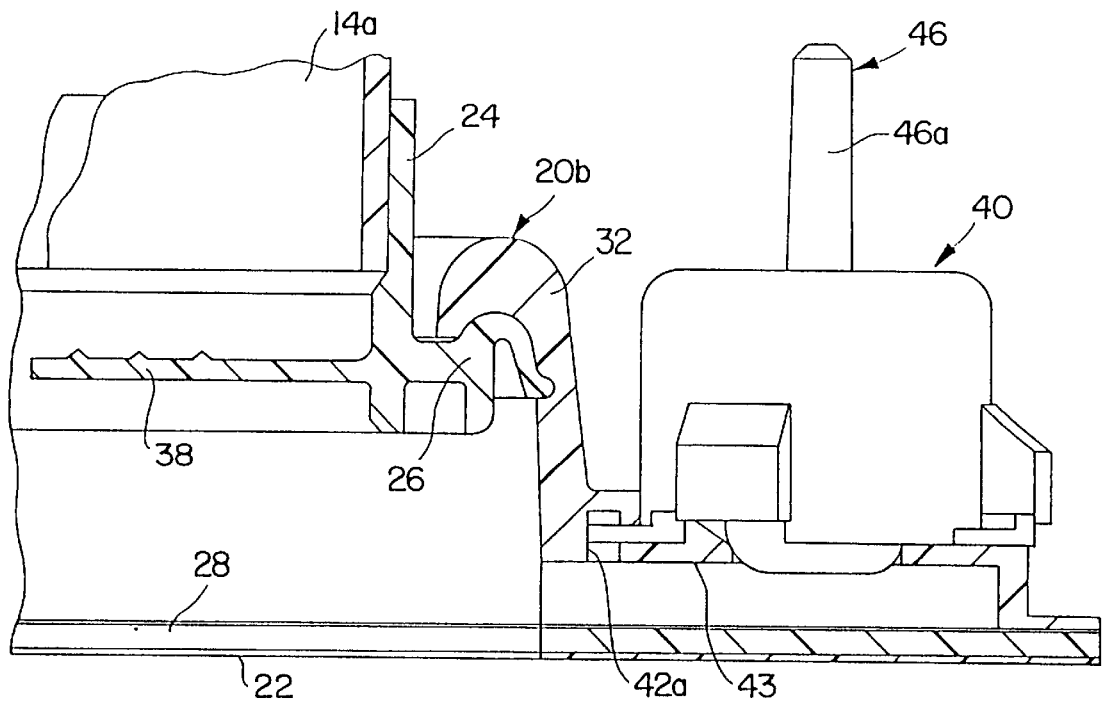
FIG. 3 is a more detailed view, partially in cross section, of a segment of a connect and disconnect assembly shown connected in the enclosure of FIG. 1.
Figure 4:
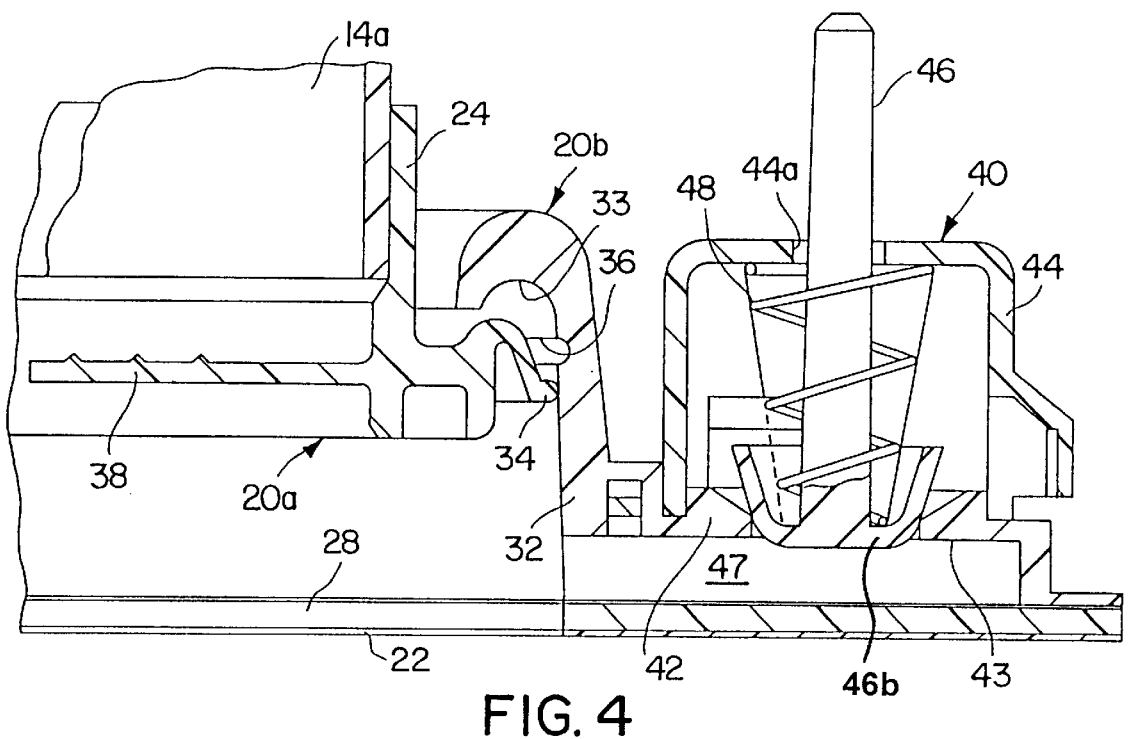
FIG. 4 is a cross sectional view like FIG. 3 but with the assembly shown partially disconnected.
Figure 5:
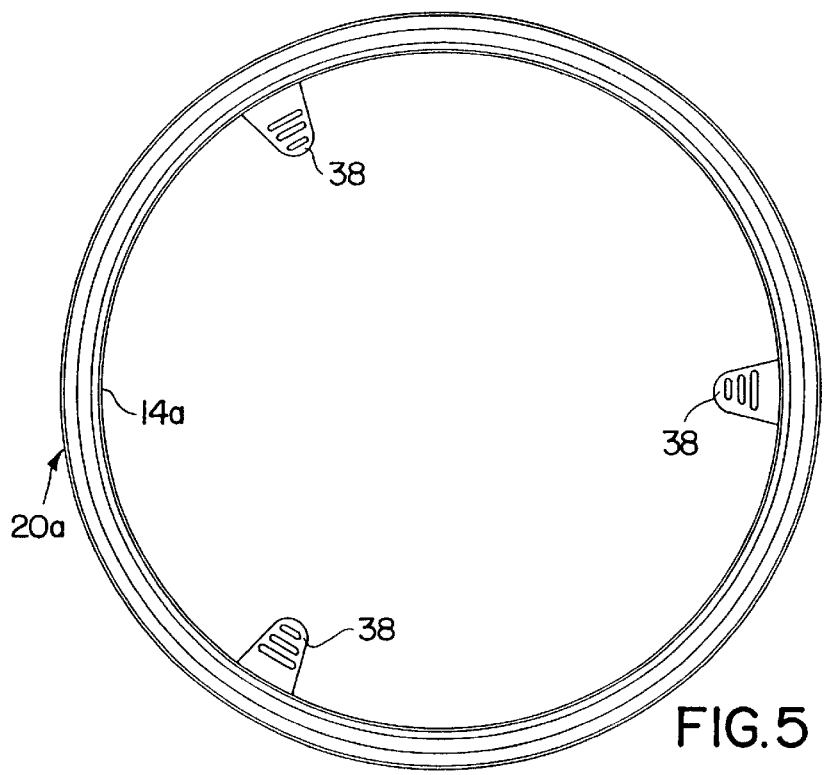
FIG. 5 is a view in cross section of an upper seal ring of the sleeve, or enclosure, taken along the line 5—5 of FIG. 2.
Figure 6:
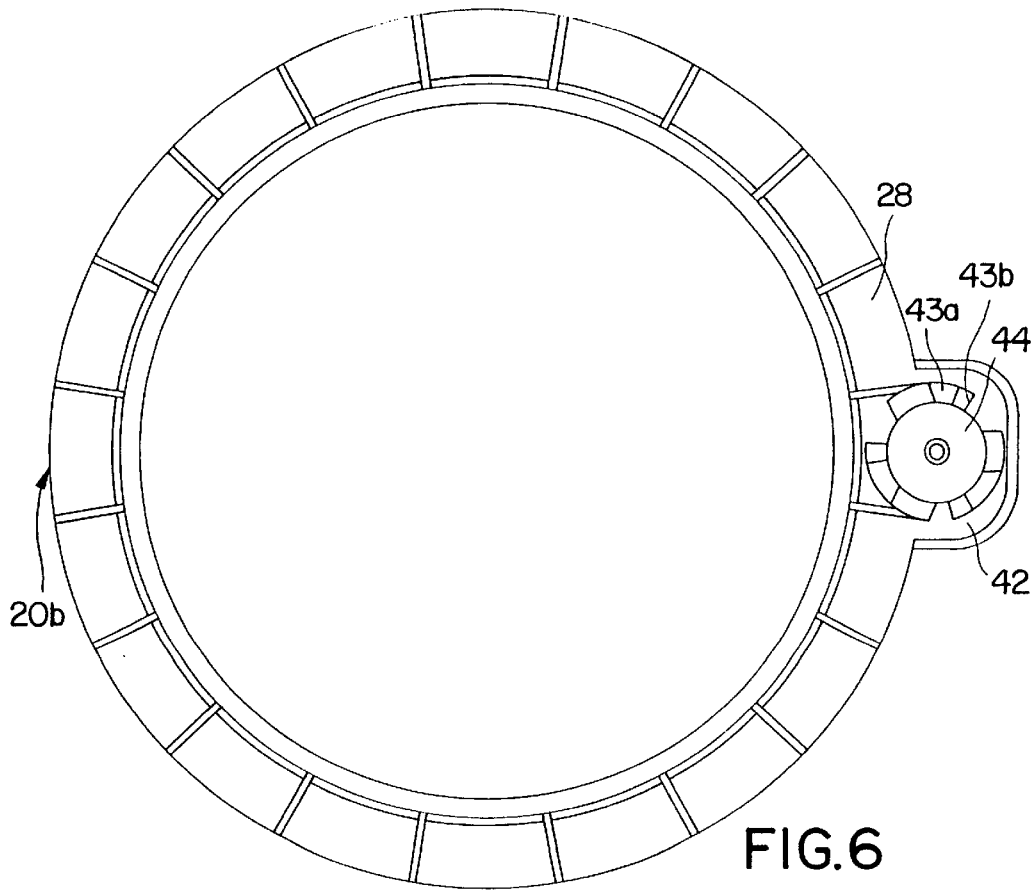
FIG. 6 is a plan view of a lower seal ring with an integral relief valve.

Lower ring 20b includes an annular flange 28 having adhesive 22 for securing ring 20b to the skin of a patient during surgery. A peel strip 30 (FIG. 2) covers the adhesive until the ring is to be applied to the skin of the abdomen. A preferred adhesive is IT8-59-A by Tolas Health Care Packaging of Feasterville, Pa. An annular member 32 sealed around its bottom to flange 28 extends upward and terminates in a downwardly facing annular groove 33 formed to interface in a tight seal with bead 26 of upper ring 20a. An annular detent 34 extending radially from bead 26 snaps into an annular groove 36 on the inner surface of member 32 when bead 26 and groove 33 are positively engaged as shown in FIG. 3. Pull tabs 38 extending inward from cylinder 24 enable the surgeon's fingers to pull detent 34 inward and disengage it from groove 36, thereby releasing upper ring 16a from lower ring 20b as shown in FIG. 4.

Lower ring 2b further includes a normally closed gas pressure relief valve 40 for limiting increases in pressure in the abdominal cavity as may be caused when the surgeon inserts his/her hand and displaces the sleeve 14. The valve 40 comprises a seat 42 integrally molded in the periphery of lower ring 20b, a cap 44, a poppet valve 46, and a helical spring 48. Cap 44 is secured to ring 16b by turning it about its cylindrical axis until tabs 43a on the bottom edge mate with slots 43b around seat 42. An aperture 44a in the top of cap 44 guides a stem 46a of plunger 46 onto seat 42 as well as serves as a vent for sufflation gas released through valve 40. Spring 48, around stem 46a between the top of cap 44 and a head 46b of plunger 46, biases valve 40 to a normally closed position. A recess 43 in the surface beneath seat 42b forms a channel 47 with flange 28 for continuously communicating between valve 40 and the abdominal cavity when lower seal ring 20b is adhered to the surface of the abdomen. If the cavity pressure exceeds a safe limit for pneumoperitoneum, e.g. 30 mm Hg, plunger 46 lifts off of seal 42 against the force of spring 48 to release the gas to ambient atmosphere. The materials of construction for cap 44 and plunger 46 are preferably a rigid thermoplastic polycarbonate of Shore 80C hardness.

Figure 10:
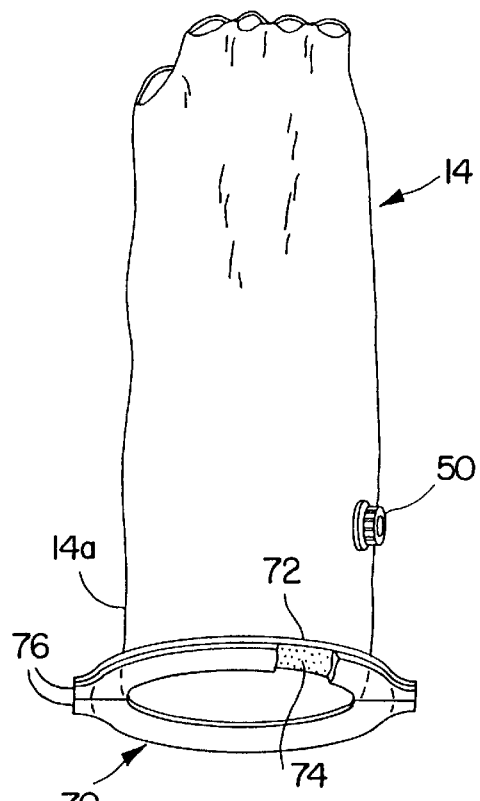
FIG. 10 is a perspective view of an enclosure, or sleeve, similar to the embodiment of FIG. 1, but utilizing a simplified connect and disconnect assembly.
Figure 11:
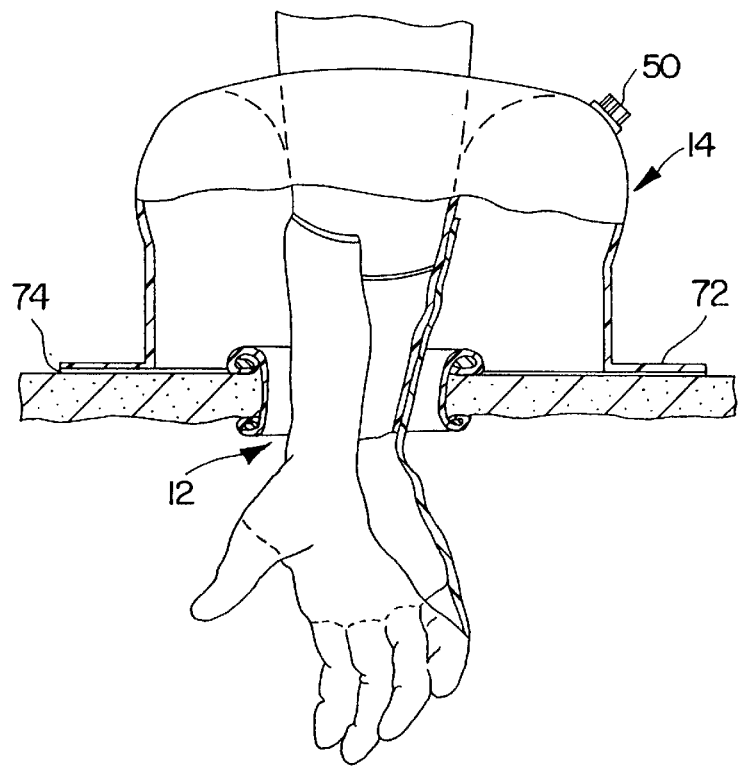
FIG. 11 is a partially-sectioned elevational view showing the enclosure, or sleeve, of FIG. 10 reversely turned and in use in an operating position.

FIGS. 10 and 11 illustrate a simplified annular assembly means 70 for securing sleeve 14 directly to a patient. The assembly 70 includes a annular flange 72 of flexible plastic permanently heat-sealed or bonded around the proximal end of sleeve cuff section 14a. An adhesive 74 is coated on the bottom side of flange 72 for applying either directly to the patient's skin, or to a surgical drape, around the site of the incision. Complementary peelable strips 76 around respective halves of the flange cover the adhesive until the glove is ready for attachment to the skin or drape. A boss, that may mount either a pressure relief valve 40, as previously discussed, or provide a sealed instrument port 50, as will be discussed, may be provided in the sleeve 14 adjacent its proximal end as shown in FIG. 10. A preferred material for flange 72 is a 4 mil plastic laminate of EVA/Surlyn®/EA, and a preferred adhesive is IT8-59-A supra.

Figure 7:
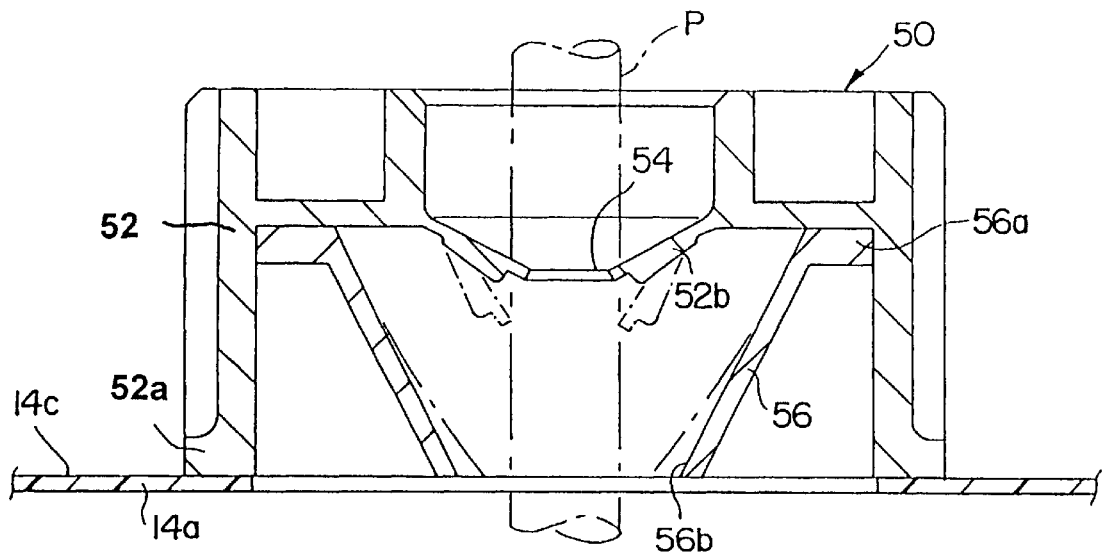
FIG. 7 is a view in cross section of an instrument port shown in the enclosure of FIG. 1.
Figure 8:
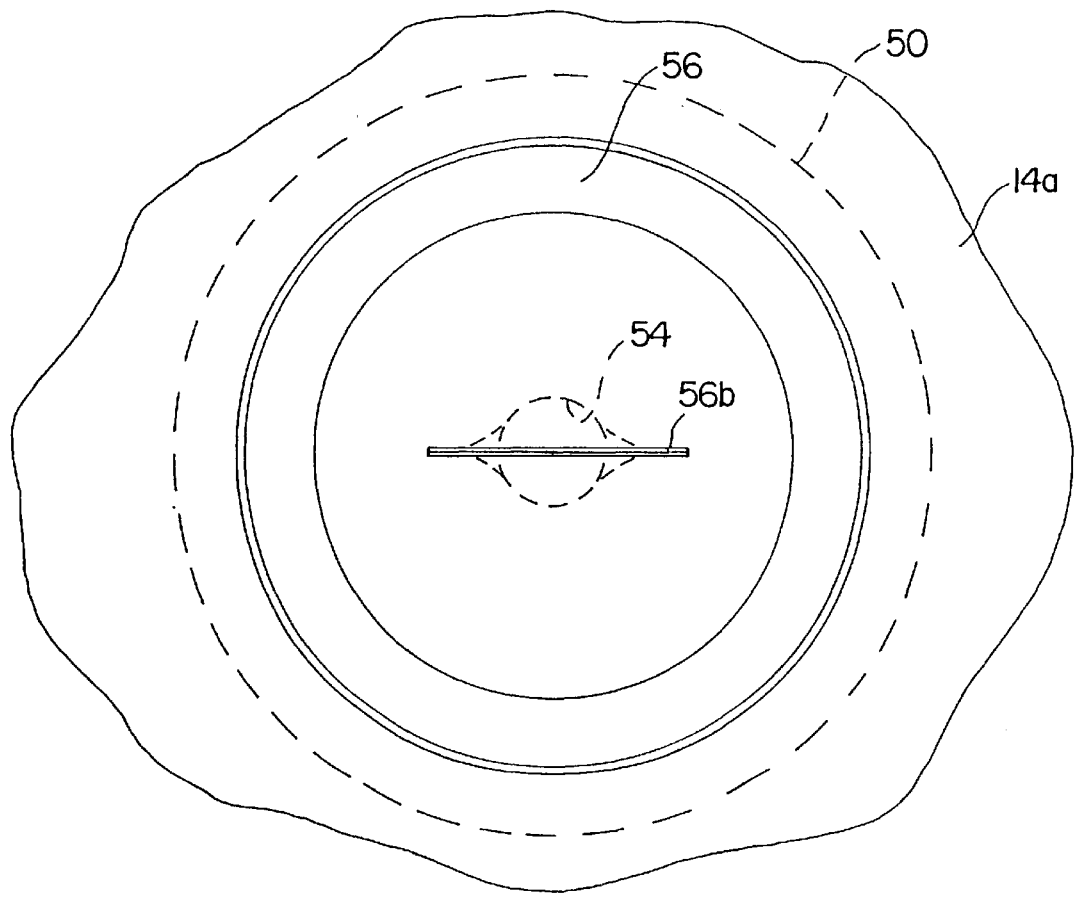
FIG. 8 is a view of the instrument port of FIG. 7 view from within the enclosure of FIG. 1.

Sleeve 14 includes an instrument port 50 located close to the proximal end of cuff section 14a to provide an optional entry into the abdominal cavity for instruments such as graspers, staplers, clip appliers, scopes, etc. Referring to FIGS. 7 and 8, port 50 includes a generally cylindrical housing 52 with a first flanged base 52a at one end secured to the inner side 14c of cuff section 14a. The other end defines a cone-shaped wall 52b tapering along its conical axis into the housing to a circular hole 54 at the small end which is sized for slidably receiving an instrument without leakage. A duckbill check valve 56 prevents pressure loss when no instrument is present in port 50. The duckbill check valve 56 comprises a second flanged base 56a at one end secured to the inside of the housing 52 adjacent to wall 52b. The other end tapers to a normally closed slit 56b spaced below hole 54 in a plane transverse to the conical axis of wall 52b. Housing 52 and insert 56 have sufficient resilience for wall 52b to form a gas-tight seal around the instrument's surface and to ensure that slit 56b closes tightly after the instrument is withdrawn. A suitable material found for this purpose is a molded thermoplastic rubber such as Santoprene® by Advanced Elastomer Systems.

Figure 9:
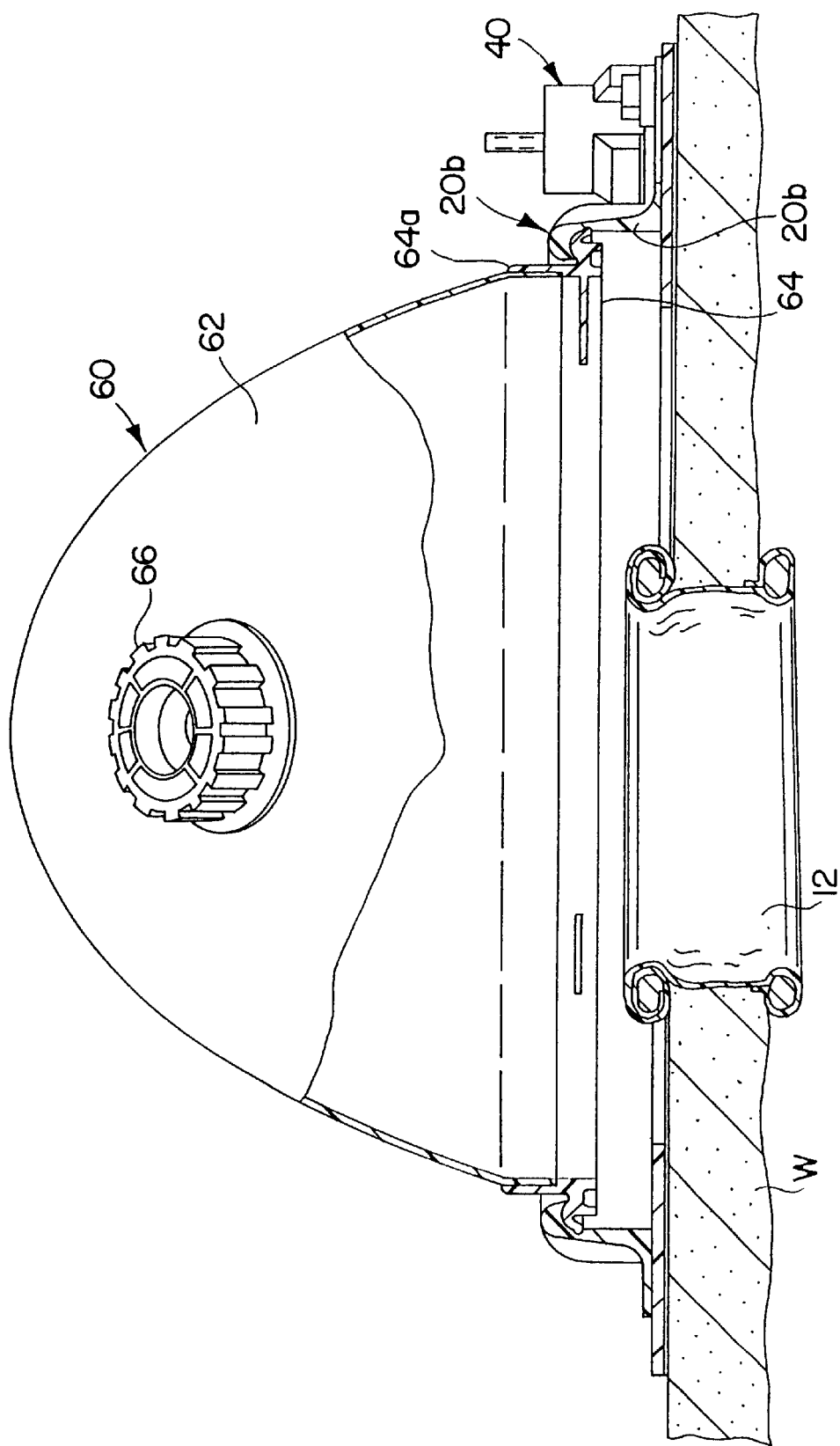
FIG. 9 is a view in elevation and partial cross section of an extracorporeal pneumoperitoneum enclosure according to another embodiment of the invention as applied during an interruption of a surgical procedure.

FIG. 9 illustrates an alternate embodiment of an extended pneumoperitoneum enclosure 60 according to the invention for use in place of the glove enclosure 10 during interruptions in surgery conducted under pneumoperitoneum conditions. It comprises a hemispheric dome-shaped envelope 62 of thin transparent flexible polyethylene film and an upper seal ring 64 of like construction as upper seal ring 20a. The perimeter at the open base is sealed around upper seal ring 64 and interconnects with lower seal ring 20b of assembly 20. Of course, enclosure 60 may also include its own lower seal ring such as utilized in the FIGS. 10 and 11 embodiment. Access by surgical instruments is provided by an instrument port 66, like port 50, secured to envelope 62.

A method according to the invention for performing hand-assisted abdominal laparoscopic surgery utilizing the extended pneumoperitoneum enclosures as above-described will now be described.

The site for making the incision is precisely traced on the abdomen of the patient. In the embodiment of FIGS. 1–8, seal ring 20b and sleeve 14 are preferably separated from upper seal ring 20a and placed on the surgeon's hand before ring 20a is attached to the abdomen in order to afford a more clear unobstructed view of the tracing. Peel strip 30 covering adhesive 22 on lower ring 20b is removed and the ring adhered to the abdomen around the tracing.

Guided by the tracing, a small muscle-splitting incision is made through the abdomen wall sufficient in size to allow the surgeon's hand to pass through. The peritoneum is incised roughly the same amount. Wound liner and retractor 12 is installed in the incision to protect the wound from contamination and to spread it apart for easier access by the hand. The abdomen wall and peritoneum may also be punctured at other locations for receiving an insufflator, a laparoscope and other instruments.

Wearing an inner surgical glove 16, the surgeon dons sleeve 14 by placing his/her hand into fingerless hand section 14b until the thumb and fingers extend completely through holes 15 and become snugly sealed thereby. Cuff section 14a and upper ring 20a (or assembly 70 of FIG. 10) are drawn up over the forearm exposing the outer side 14d of fingerless section 14a. For added protection against leakage around holes 15, an outer surgical glove 18 is preferably placed over the exposed finger portions of inner glove 16 and hand section 14a. If preferred, the surgeon may don the sleeve 14 and attach it to the lower ring 20b before incising the abdomen.

The sleeve 14 is then reversely turned on itself with the cuff section 14a inverted and upper ring 20a is sealed in lower ring 16b by pressing bead 26 into recess 33 until detent 36 of upper ring 20a snaps into groove 36 of lower ring 20b. The abdominal cavity and the annular envelope formed by sleeve 14 may now be insufflated to the desired pressure either through a separate cannula or through port 50 in sleeve 14. The thus-covered surgeon's hand may thereafter enter and re-enter the abdominal cavity as often as necessary during the surgery without losing pneumoperitoneum. Any increase in insufflating gas pressure, such as caused by a reduction in volume inside the sleeve-formed chamber surrounding the surgeon's forearm when inserting the hand, is relieved by pressure relief valve 40.

Should an extended interruption in a surgical procedure be needed while still maintaining pneumoperitoneum, sleeve 14, attached to upper seal ring 20a, may be disconnected leaving in place lower seal ring 20b. Dome-shaped envelope 62, attached to upper seal ring 64, may then be connected to lower seal ring 20b and insufflation restored.

Of course, when using the embodiment of FIGS. 10 and 11, the surgeon would don the sleeve 14, as described above, peel strips 76 from the adhesive 74 and place the flange directly on the skin or surgical drape around the incision site after the wound liner and retractor 12 has been installed.

Some of the many advantages and novel features of the invention should now be readily apparent. For example, an extracorporeal pneumoperitoneum enclosure is provided which can be continually worn by the surgeon during hand-assisted laparoscopic surgery under conditions of pneumoperitoneum without loss of free hand and finger movement. It allows the surgeon to quickly disconnect and reconnect the enclosure from the patient while still retaining it on his/her hand. An alternate embodiment provides a dome-like enclosure which can be substituted for the sleeve whenever a protracted interruption in a surgical procedure is necessary. It enables minimal invasive surgery and risk of damage to a patient's immune system. Due to the smaller incisions, shorter healing time and less time for recuperation in the hospital is possible. The enclosures are also relatively simple in design and easy to use.

It will be understood, of course, that various changes in the details, materials, steps and arrangement of parts which have been herein described and illustrated in order to explain the nature of the invention may be made by those skilled in the art within the principle and scope of the invention as expressed in the appended claims.

What is claimed is:

1. Apparatus for use in providing extracorporeal pneumoperitoneum around a surgical incision in a patient, comprising:

an elongate flexible sleeve (14) having a distal end portion (14b) for covering a surgeon's hand, an intermediate portion for covering the surgeon's forearm, and a proximal portion (14a) having an end opening enabling insertion of the surgeon's hand and forearm, and means for releasably gas-tightly securing said proximal portion (14a) end opening to the patient around the surgical incision and enabling said intermediate portion to be reversely turned to extend along the surgeon's forearm when said sleeve (14) is operatively secured to the patient and insufflated;

said distal portion (14b) of said flexible sleeve (14) having a plurality of openings (15) for receiving a surgeon's fingers and thumb; and said sleeve (14) being formed of supple plastic which conforms, but does not continuously constrict, about the bases of the fingers and thumb when the sleeve is installed and the surgeon's hand clasped.

2. Apparatus according to claim 1, wherein said plastic material is a polyethylene film.

3. Apparatus for use in providing extracorporeal pneumoperitoneum around a surgical incision in a patient, comprising:

an elongate flexible sleeve (14) having a distal end portion (14b) for covering a surgeon's hand, an intermediate portion for covering the surgeon's forearm, and a proximal portion (14a) having an end opening enabling insertion of the surgeon's hand and forearm, and means for releasably gas-tightly securing said proximal portion (14a) end opening to the patient around the surgical incision and enabling said intermediate portion to be reversely turned to extend along the surgeon's forearm when said sleeve (14) is operatively secured to the patient and insufflated, said distal portion (14b) of said flexible sleeve (14) having a plurality of openings (15) for receiving a surgeon's fingers and thumb, and the diameters of said openings (15), in inches, being as follows: thumb 0.98, index finger 0.79, middle finger 0.87, ring finger 0.75 and pinky 0.63.

4. Apparatus for use in providing extracorporeal pneumoperitoneum around a surgical incision in a patient, comprising:

an elongate flexible sleeve (14) having a distal end portion (14b) for covering a surgeon's hand, an intermediate portion for covering the surgeon's forearm, and a proximal portion (14a) having an end opening enabling insertion of the surgeon's hand and forearm, and means for releasably gas-tightly securing said proximal portion (14a) end opening to the patient around the surgical incision and enabling said intermediate portion to be reversely turned to extend along the surgeon's forearm when said sleeve (14) is operatively secured to the patient and insufflated, said means including an annular base (20b) adapted to be adhesively secured to the patient around the incision and an annular ring (20a) connected to said sleeve (14) and releasably engageable with said base (20b), and said annular base (20b) having a pressure relief valve (40) for relieving overpressures above about 30 mm Hg.

5. Apparatus according to claim 4, wherein said annular ring (20a) matingly engages interiorly of said base (20b) in gastight relation therewith.

6. Apparatus according to claim 4, wherein said annular ring (20a) has at least one inwardly-extending pull tab (38) affording disengagement of said annular ring (20a) from said annular base (20b).

7. Apparatus according to claim 4, wherein said pressure relief valve (40) has a cap (44) with an aperture (44a), a plunger (46) with a head (46b) confined by said cap (44) and a stem (46a) extending through and beyond said aperture (44a) for being guided by said aperture (44a), and a spring (48) extending about said stem (46a) between said head (46b) and cap (44).

8. Apparatus according to claim 9, wherein said annular ring (20a) has at least one inwardly-extending pull tab (38) affording disengagement of said annular ring (20a) from said annular base (20b).

9. Apparatus for use in providing extracorporeal pneumoperitoneum around a surgical incision in a patient, comprising:

an elongate flexible sleeve (14) having a distal end portion (14b) for covering a surgeon's hand, an intermediate portion for covering the surgeon's forearm, and a proximal portion (14a) having an end opening enabling insertion of the surgeon's hand and forearm, means for releasably gas-tightly securing said proximal portion (14a) end opening to the patient around the surgical incision and enabling said intermediate portion to be reversely turned to extend along the surgeon's forearm when said sleeve (14) is operatively secured to the patient and insufflated, said means including an annular base (20b) adapted to be adhesively secured to the patient around the incision and an annular ring (20a) connected to said sleeve (14) and releasably engageable with said base (20b), and a closure (60) releasably engageable with said base (20b) affording selective sealed connection thereto of either said sleeve (14) or said closure (60).

10. Apparatus according to claim 9 wherein said closure (60) includes a flexible hemispheric dome (62) overlying said base ring (20b).

11. Apparatus according to claim 10 wherein said closure (60) includes a port (66) having an interiorly-opening duckbill check valve (56) affording passage of a surgical instrument into the closure (60).

12. Apparatus for use in providing extracorporeal pneumoperitoneum around a surgical incision in a patient, comprising:
- an elongate flexible sleeve (14) having a distal end portion (14b) for covering a surgeon's hand, an intermediate portion for covering the surgeon's forearm, and a proximal portion (14a) having an end opening enabling insertion of the surgeon's hand and forearm, said distal portion (14b) having a plurality of openings (15) for receiving a surgeon's fingers and thumb,
- means for releasably gas-tightly securing said proximal portion (14a) end opening to the patient around the surgical incision and enabling said intermediate portion to be reversely turned to extend along the surgeon's forearm when said sleeve (14) is operatively secured to the patient and insufflated,
- an outer surgical glove (18) applied on said surgeon's hand after being operatively inserted into said distal portion (14b) of said sleeve and through said openings (15) for ensuring sealed closure of said openings (15), and
- an inner surgical glove (16) disposed on the surgeon's hand inwardly adjacent said sleeve distal portion (14b) for cooperating with said outer surgical glove (18) to sandwich said sleeve distal end (14b) therebetween.

13. Apparatus for preventing over-insufflation of a body cavity during endoscopic surgery, comprising:
- a flexible sleeve (14) having one end portion (14a) operatively sealingly connected to a patient around an incision and another end portion (14b) operatively sealingly connected to a surgeon,
- a pressure relief valve (40) having an inlet in gas communication with the interior of said sleeve (14) and having an outlet to ambient atmosphere, and
- means for biasing said pressure relief valve (40) into a closed position normally blocking flow from the inlet to the outlet until a predetermined pressure level is reached within said sleeve (14) at which time said pressure relief valve permits gas to flow from said inlet to said outlet, whereby over-insufflation of the body cavity can be avoided during endoscopic surgical movements of the surgeon.

14. Apparatus according to claim 13, wherein said pressure relief valve (40) has a cap (44) with an aperture (44a) and a plunger (46) with a head (46b) confined by said cap (44) and a stem (46a) extending through and beyond said aperture (44a) for being guided by said aperture (44a), and wherein said means for biasing said pressure relief valve (40) is a spring (48) extending about said stem (46a) between said head (46b) and cap (44).

15. Apparatus according to claim 13 wherein said pressure relief valve (40) includes a base (20b) releasably connectable to the patient in proximity with the incision.

16. Apparatus according to claim 15 wherein said base (20b) is formed integral with a ring surrounding said incision and adhesively securable to the patient.

17. Apparatus according to claim 13 wherein said predetermined pressure is less than about 30 mm Hg.

18. Apparatus according to claim 16 including a closure (60) having a self-sealing instrument port (66), said closure (60) being releasably engageable with said ring (20b) for affording selective engagement of either said closure (60) or said sleeve (14) on said ring (20b).

19. Apparatus according to claim 13 wherein said flexible sleeve (14) has an intermediate portion reversely turned on itself to form a variable volume annular chamber around the surgeon's forearm.

20. Apparatus for providing extracorporeal pneumoperitoneum around a surgical incision, comprising:
- a flexible gas impermeable envelope (14) having a proximal section (14a) defining a proximal end opening, a distal section (14b) with holes (15) for receiving a surgeon's digits, and an intermediate section reversely turnable about the surgeon's forearm with the distal section (14b) telescopically moveable into the proximal section (14a);
- ring means (20) carried by said envelope (14) about said proximal end opening for securing said envelope (14) in sealing contact with skin around the incision; and
- a pressure relief valve (40) carried by said ring means (20) for communicating with said envelope (14) to vent insufflated gas when its pressure exceeds a pre-selected limit.

21. Apparatus according to claim 20, wherein said pressure relief valve (40) has a cap (44) with an aperture (44a), a plunger (46) with a head (46b) confined by said cap (44) and a stem (46a) extending through and beyond said aperture (44a) for being guided by said aperture (44a), and a spring (48) extending about said stem (46a) between said head (46b) and cap (44).

22. Apparatus according to claim 23, wherein said ring (20a) mounted on said envelope proximal end has at least one inwardly-extending pull tab (38) affording disengagement of said ring (20a) from said other ring (20b).

23. Apparatus according to claim 20 wherein said ring means (20) includes releasably matingly engageable rings (20a, 20b), one mounted on said envelope proximal end and the other adhesively connectable to said skin.

24. Apparatus according to claim 23 including a closure (60) having a ring (64a), like in construction to said one ring, for enabling said closure (60) to be selectively mounted onto said skin adhered ring.

25. Apparatus according to claim 24 including:
- a bead (26) formed in said one ring around said envelope proximal end opening; and
- a groove (33) formed in said other ring for interengaging said bead (26).

26. Apparatus according to claim 25 further comprising:
- detent means (34, 36) formed in said rings for interlocking when said bead (26) and said groove (33) are fully engaged.

27. Apparatus according to claim 20, wherein said preselected pressure limit is approximately 30 mm Hg.

28. Apparatus according to claim 20 further comprising:
- a port (50) fixed to said envelope (14) and formed to admit a surgical instrument while maintaining extracorporeal pneumoperitoneum.

29. Apparatus according to claim 28 wherein said port means (50) further includes:
- a generally cylindrical housing (52) having a conical wall (52b) tapering inward to form a circular hole (54) for slidably receiving said surgical instrument;
- a duckbill check valve (56) secured to said housing (52) and having a normally closed slit spaced below said hole (54) in a plane transverse to a conical axis of said wall (52b) for slidably receiving the instrument in series with said hole (54).

30. Apparatus according to claim 29 wherein:
- said housing (52) has sufficient resilience for said hole (54) to form a gas-tight seal around the instruments' surface; and said duckbill check valve (56) has sufficient resilience for said slit to close tightly upon itself when the instrument is withdrawn therefrom.

31. Apparatus for hand-assisted minimally invasive surgery under conditions of pneumoperitoneum, comprising:

a gas impermeable flexible sleeve (14) having a fingerless distal hand section (14b) terminating in holes (15) for receiving the thumb and fingers of a surgeon's hand, an intermediate cuff section extending from said distal hand section (14b), and a proximal end section (14a) terminating in an opening, said intermediate cuff section being reversely turnable on itself for extending along the surgeon's forearm when the proximal end opening (14a) is displaced toward the distal end (14b), a peelable adhesive ring (20b) carried by said sleeve (14) for sealing contact with skin around an abdominal incision; and means for releasably coupling said adhesive ring (20b) to said sleeve (14) about its proximal end opening.

32. Apparatus according to claim 31 wherein said releasable coupling means includes a first ring (20a) sealed to said sleeve (14) about its proximal end opening for releasably sealingly engaging interiorily of said adhesive ring (20b).

33. Apparatus according to claim 31 including pressure relief valve means (40) carried by said adhesive ring (20b) for relieving pressure above a predetermined level occurring inside said reversely turned sleeve (14).

34. Apparatus according to claim 31 including an outer surgical glove (18) encasing the surgeon's hand after insertion through the distal end holes (15) for effecting a positive seal of the holes (15).

35. Apparatus according to claim 34 including an inner surgical glove (16) encasing the surgeon's hand interiorily of the sleeve (14) for sandwiching the sleeve distal end (14b) between inner and outer surgical gloves (16, 18).

36. Apparatus according to claim 32, wherein said first ring (20a) has at least one inwardly-extending pull tab (38) affording disengagement of said first ring (20a) from said adhesive ring (20b).

37. Apparatus according to claim 33, wherein said pressure relief valve means (40) has a cap (44) with an aperture (44a), a plunger (46) with a head (46b) confined by said cap (44) and a stem (46a) extending through and beyond said aperture (44a) for being guided by said aperture (44a), and a spring (48) extending about said stem (46a) between said head (46b) and cap (44).

* * * * *